(12) United States Patent
Lang

(10) Patent No.: US 9,173,680 B2
(45) Date of Patent: Nov. 3, 2015

(54) SEAL FOR A TROCAR SLEEVE AND SUCH TROCAR SLEEVE

(75) Inventor: Dieter Lang, Stockheim (DE)

(73) Assignee: Karl Storz GmbH & Co. KG (DE)

( * ) Notice: Subject to any disclaimer, the term of this patent is extended or adjusted under 35 U.S.C. 154(b) by 1123 days.

(21) Appl. No.: 11/744,061

(22) Filed: May 3, 2007

(65) Prior Publication Data

US 2007/0260186 A1 Nov. 8, 2007

(30) Foreign Application Priority Data

May 3, 2006 (DE) .......................... 10 2006 021 974

(51) Int. Cl.
*A61B 1/00* (2006.01)
*A61M 5/178* (2006.01)
*A61B 17/34* (2006.01)
*A61M 39/06* (2006.01)

(52) U.S. Cl.
CPC .......... *A61B 17/3498* (2013.01); *A61B 17/3423* (2013.01); *A61B 17/3462* (2013.01); *A61B 2017/3464* (2013.01); *A61M 39/0613* (2013.01)

(58) Field of Classification Search
CPC ........... A61B 17/3498; A61B 17/3423; A61B 17/3462; A61B 2017/3464; A61M 39/0613
USPC ................. 604/167.01, 164, 256, 26
See application file for complete search history.

(56) References Cited

U.S. PATENT DOCUMENTS

| | | | |
|---|---|---|---|
| 2,294,101 A * | 8/1942 | Tripp ......................... | 49/495.1 |
| 3,295,547 A | 1/1967 | Scaramucci | |
| 3,301,443 A | 1/1967 | Clancy et al. | |
| 3,628,565 A | 12/1971 | McWethy | |
| 4,430,081 A | 2/1984 | Timmermans | |
| 4,909,798 A * | 3/1990 | Fleischhacker et al. ...... | 604/256 |
| 5,122,122 A | 6/1992 | Allgood | |
| 5,496,280 A * | 3/1996 | Vandenbroek et al. .. | 604/167.03 |
| 5,634,937 A * | 6/1997 | Mollenauer et al. .......... | 606/213 |
| 5,685,854 A | 11/1997 | Green et al. | |
| 5,782,817 A * | 7/1998 | Franzel et al. ................ | 604/256 |

(Continued)

FOREIGN PATENT DOCUMENTS

| | | |
|---|---|---|
| DE | 7430345 | 12/1974 |
| DE | 37 37 121 A1 | 5/1989 |

(Continued)

OTHER PUBLICATIONS

Derwent English Abstract of German Patent DE 3737121 A1, Staeblein, Alexander, 1989.*

(Continued)

*Primary Examiner* — Richard Louis

(74) *Attorney, Agent, or Firm* — Whitmyer IP Group LLC

(57) ABSTRACT

A seal for a trocar sleeve comprises a sealing body which, in the direction of a longitudinal center axis of the sealing body, has a first axial end and a second axial end and, between said first and second ends, an elastic sealing element which, in a radially inner area relative to the longitudinal center axis, defines a passage for an instrument. Said sealing element has a substantially tubular hollow space whose radially inner wall area annularly surrounds the passage, and said hollow space contains a fluid and and has a radially inner wall area annularly surrounding the passage, and a radially outer wall area on a radially outer side of the hollow space, the radially outer wall area having a wall thickness larger than a wall thickness of the radially inner wall area.

21 Claims, 5 Drawing Sheets

(56) References Cited

U.S. PATENT DOCUMENTS

| | | | |
|---|---|---|---|
| 5,788,676 A | 8/1998 | Yoon | 604/167 |
| 5,989,224 A * | 11/1999 | Exline et al. | 604/167.02 |
| 6,171,299 B1 * | 1/2001 | Bonutti | 606/1 |
| 6,276,661 B1 | 8/2001 | Laird | 251/61.1 |
| 7,470,255 B2 * | 12/2008 | Stearns et al. | 604/167.06 |
| 2002/0010424 A1 * | 1/2002 | Dennis et al. | 604/167.03 |
| 2003/0195541 A1 * | 10/2003 | Exline et al. | 606/185 |
| 2005/0059934 A1 * | 3/2005 | Wenchell et al. | 604/167.01 |
| 2005/0261661 A1 | 11/2005 | McFarlane | 604/506 |
| 2006/0020281 A1 * | 1/2006 | Smith | 606/167 |

FOREIGN PATENT DOCUMENTS

| | | |
|---|---|---|
| DE | 9109909.9 U1 | 11/1991 |
| DE | 9112550.2 U1 | 1/1992 |
| DE | 4306205 C1 | 10/1994 |
| DE | 692 04 958 T2 | 3/1996 |
| EP | 0316096 A2 | 5/1989 |
| EP | 0323018 A2 | 7/1989 |
| EP | 0521590 A1 | 1/1993 |
| EP | 0 538 060 B1 | 4/1993 |
| EP | 0567141 A2 | 10/1993 |
| FR | 1592547 | 6/1970 |
| FR | 2863504 A1 | 6/2005 |
| GB | 2065479 A | 7/1979 |
| WO | 9301850 A1 | 2/1993 |
| WO | 9419052 A1 | 9/1994 |
| WO | WO 99/42152 | 8/1999 |
| WO | WO 03/000145 | 1/2003 |

OTHER PUBLICATIONS

European Search Report, Oct. 25, 2007, 16 Pages.
European Search Report, Aug. 30, 2007, 5 pages.

* cited by examiner

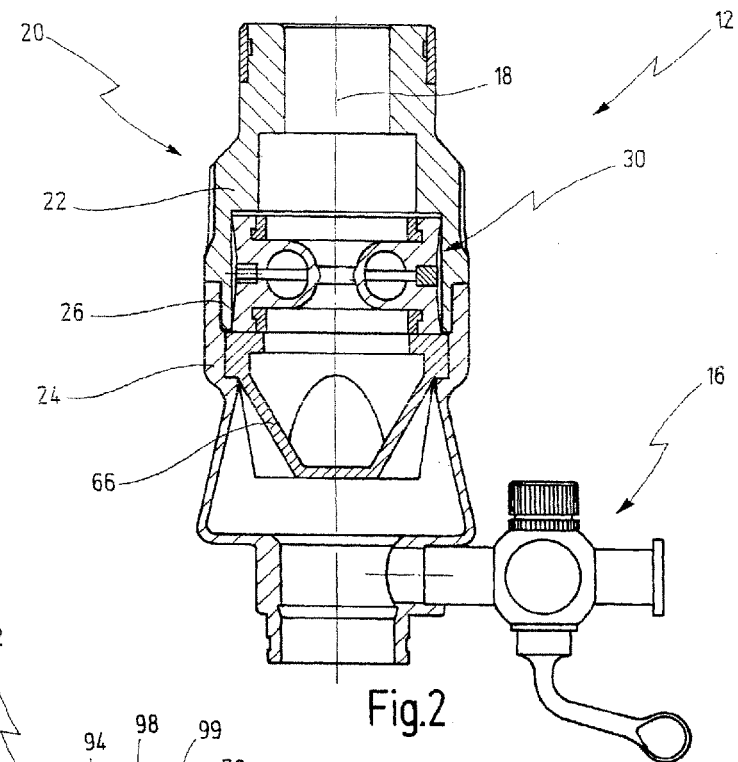
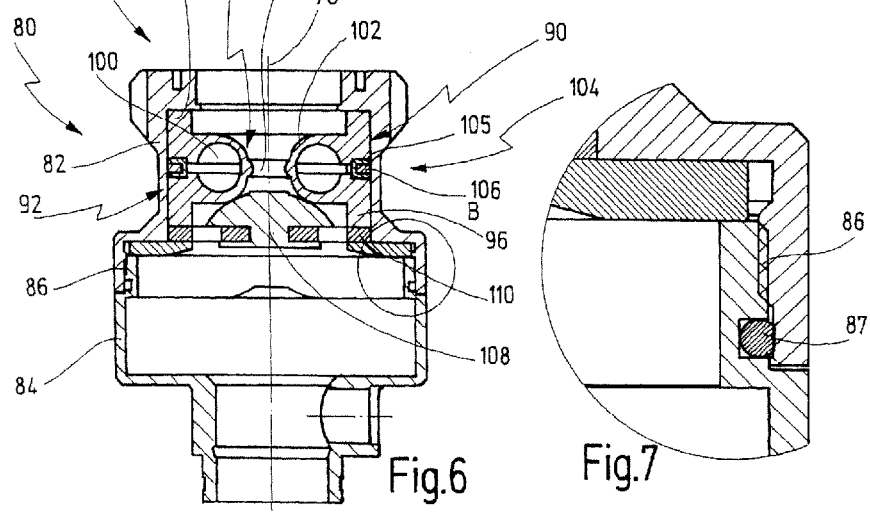

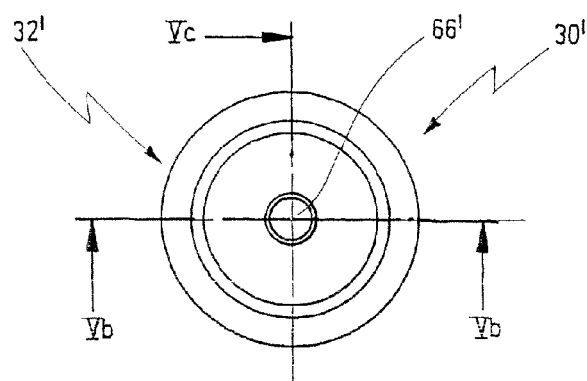
Fig.5a
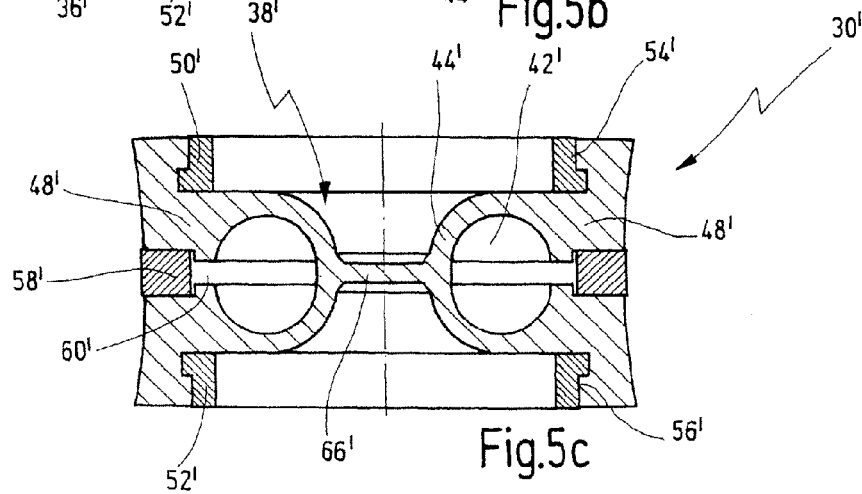
Fig.5b
Fig.5c

SEAL FOR A TROCAR SLEEVE AND SUCH TROCAR SLEEVE

CROSS REFERENCE TO RELATED APPLICATION

The present application claims priority of German Patent Application No. 10 2006 021 974.0 filed on May 3, 2006.

BACKGROUND OF THE INVENTION

The invention generally relates to seals for use in trocar sleeves.

More specifically, the invention relates to a seal for a trocar sleeve, comprising a sealing body which, in the direction of a longitudinal centre axis of the sealing body, has a first axial end and a second axial end and, between the first and second ends, an elastic sealing element which, in a radially inner area relative to the longitudinal centre axis, defines a passage for an instrument.

The invention further relates to a trocar sleeve provided with such a seal.

Trocars are used in the medical field in the context of minimally invasive surgery for introducing instruments into the human or animal body. In a minimally invasive surgical procedure, a trocar, generally consisting of a trocar sleeve and of a trocar mandrel received in the trocar sleeve, is first used to create a minimally invasive access route into a body cavity. For this purpose, the trocar is pushed with the aid of the trocar mandrel through the skin and into the body. The trocar mandrel is then withdrawn from the trocar sleeve, while the trocar sleeve is left in position in the access that has now been created. Instruments such as endoscopes, forceps, scissors, suturing tools and the like for carrying out surgical measures can now be introduced through the trocar sleeve and into the body cavity.

Several instruments with different shaft diameters are often needed during an operation. The trocar sleeve must therefore be designed accordingly for insertion of these instruments.

A further requirement of a trocar sleeve is that it seals off the body cavity from the outside when the trocar sleeve has been introduced into the body and an instrument has been introduced through the trocar sleeve. This is important particularly for use of a trocar sleeve in laparoscopy, in which the body cavity, here the abdominal space, is insufflated with a gas in order to expand the body cavity (pneumoperitoneum).

In order to seal the body cavity off from the outside when an instrument has been introduced through the trocar sleeve, such trocar sleeves comprise, in the area of the trocar head, a seal through which the respective instrument is guided. The seal for this purpose comprises an elastic sealing element that bears sealingly around the circumference of the shaft of the instrument that has been introduced.

However, since different instruments with different shaft diameters are intended to be introduced through the trocar sleeve, the seal present in the trocar sleeve must also ensure sealing for different shaft diameters of the inserted instruments. It will be appreciated that the internal diameter of the sealing element, which defines the passage for the instrument, has to be designed for the smallest shaft diameter of an instrument, so as to ensure sealing for this thin instrument too.

However, in order also to permit the introduction of instruments with a greater shaft diameter, the sealing element must possess a sufficient radially elastic extensibility. For this purpose, the presently known seals comprise sealing elements that have very thin walls. This is particularly the case of a seal known from the document DE 692 04 958 T2.

This known seal comprises a sealing element having the shape of an hourglass. The sealing element has converging and diverging side walls that form the passage for an instrument at their point of intersection. The outer ends of the seal are formed by flange sections. Said document proposes increasing the internal diameter of the passage by applying a vacuum or a negative pressure to the outside of the sealing element. However, producing a trocar sleeve seal to which a vacuum can be applied is technically complex and therefore disadvantageous.

A further disadvantage of the abovementioned thin-walled sealing elements of the known seals is that the thin wall of the sealing element can already be damaged upon initial contact with pointed, sharp or hook-shaped instruments.

A further disadvantage is that instruments with smaller shaft diameters are poorly guided in the seal.

Moreover, the sealing action of the known seals is often lost when the instrument guided through the trocar sleeve is moved sideways, i.e. transverse to the shaft direction, or tilted. Because of the poor lateral hold of the thin-walled sealing elements, a sideways movement causes the contact between the sealing element and the instrument shaft to be lost around part of the circumference of the instrument shaft, as a result of which sufficient sealing is then no longer guaranteed.

A seal known from the document DE 37 37 121 A1 also comprises a thin-walled sealing element, wherein the sealing element has a hollow space which is filled with a gaseous or liquid medium in order to narrow the passage for the instruments to be sealed, in order to obtain the desired sealing effect. This known seal thus requires an increased pressure in the hollow space of the sealing element for obtaining the sealing effect, which increased pressure is obtained by supplying a liquid or a gas into the hollow space. The disadvantage is that the trocar has to be connected with a pressure source via one or several lines during a surgical operation, which may represent an obstacle to the physician during a surgical operation. Furthermore, the expenditure in terms of additional equipment for supplying pressure to the sealing element is increased in disadvantageous fashion.

SUMMARY OF THE INVENTION

The object of the invention is therefore to develop a seal of the type mentioned at the outset in such a way that it guarantees sufficient sealing, particularly for different diameters of the instruments used, without increasing the expenditure in terms of additional equipment.

According to an aspect of the invention, a seal for a trocar sleeve is provided, comprising a sealing body having a longitudinal center axis, a first axial end and a second axial end in direction of the longitudinal center axis, and an elastic sealing element arranged between the first and second ends, the sealing element defining a passage for an instrument in a radially inner area relative to the longitudinal center axis, the sealing element further having a substantially tubular hollow space containing a fluid and having a radially inner wall area annularly surrounding the passage, and a radially outer wall area on a radially outer side of the hollow space, the radially outer wall area having a wall thickness larger than a wall thickness of the radially inner wall area.

The sealing element of the seal according to the invention accordingly has a substantially tubular elastic hollow body that contains a fluid, which can be gaseous or liquid. The tubular configuration of the sealing element has the effect that, when an instrument is guided through the sealing element, the tubular hollow space is radially compressed, as a result of which the area of contact of the sealing element on the instrument shaft also has an axial extent. In the case where the hollow space is tightly sealed off, for which provision can be made, the fluid contained in the hollow space is compressed upon the radial compression of the hollow space and applies a corresponding counter-pressure to the instrument shaft, thus ensuring that the sealing element at all times bears tightly on the instrument shaft about the full circumference. The hollow space is compressed to a greater or lesser degree depending on the shaft diameter of the inserted instrument.

The design of the sealing element as a substantially tubular hollow body containing a fluid also has the advantage that, in the event of a radially directed movement of the inserted instrument, the fluid that is displaced during this movement at one site exerts an increased pressure on the radially inner wall area of the sealing element in the opposite area of the hollow space, such that the radially inner wall area at the site of increased pressure is even extended radially inwards, as a result of which, in the event of a sideways movement of the instrument shaft, the sealing element at all times bears tightly on the instrument shaft about the full circumference. The same applies in the event of the instrument being tilted relative to the sealing element.

Due to the fact that the radially outer wall area of the sealing element has a wall thickness which is larger than the wall thickness of the radially inner wall area, the radially outer wall area exerts a counterforce which is directed radially inward when an instrument is introduced through the sealing element, so that a sufficient sealing between the introduced instrument and the radially inner sealing wall is obtained without the hollow space of the seal having to be filled with a gas or a liquid for obtaining an overpressure, in order to obtain this sealing effect. The seal according to the invention thus does not require a connection to an air or liquid source which, on the one hand, keeps the expenditure in terms of additional equipment low, and, on the other hand, obstacles like pipes or lines are avoided in the operating field.

In the radial direction, i.e. transverse to the longitudinal centre axis of the sealing body, the hollow space can preferably have a maximum internal diameter corresponding to the greatest diameter of the instruments used.

In a preferred embodiment, the fluid is a gas, in particular air.

The use of a gas as the fluid has the advantage that a gas is compressible, such that the hollow space has elastic properties in the manner of a pneumatic spring. The gas used is preferably air, and the air can be enclosed in the hollow space by simple means during the production of the seal. In particular however, according to an embodiment to be described further below, it is also possible for the hollow space not to be closed off in an inherently airtight manner, and instead it can have a certain lack of leaktightness, permitting an escape of the fluid in the case of large shaft diameters. When using air as the fluid, the hollow space can then automatically refill with air from the environment during relaxation or during use of an instrument with a smaller diameter, without the seal having to be connected to a gas reservoir.

In another preferred embodiment, the fluid is a liquid, preferably an oil.

Although a liquid is less compressible than a gas, or incompressible, it is nevertheless able, in the case of smaller shaft diameters, to permit a higher counter-pressure in order to securely press the radially inner wall area onto the shaft of the inserted instrument. For larger shaft diameters, however, the fluid must be able to escape from the hollow space, for which purpose a corresponding equalizing reservoir would have to be provided.

In another preferred embodiment, the fluid is at atmospheric pressure when the sealing element is in the relaxed state.

This measure is advantageous particularly with the aforementioned embodiment in which the fluid used is air, since no complicated measures have to be taken to ensure that, in the relaxed state of the sealing element, a pressure in the hollow space is provided that is higher than the atmospheric pressure.

In another preferred embodiment, the radially inner wall area of the hollow space is bulged convexly, as seen from the longitudinal centre axis, when the sealing element is in the relaxed state.

This embodiment has the advantage of making it easier to insert instruments through the sealing element, because the passage for the instrument narrows in a funnel shape, viewed in the direction of insertion. The danger of the instrument damaging the radially inner wall area of the sealing element is thus reduced. The same applies to withdrawing the instrument from the trocar sleeve, since the passage also narrows in a funnel shape when viewed from the second end of the sealing element.

In another preferred embodiment, the hollow space is substantially O-shaped or oval in a section along the longitudinal centre axis.

In the case of an oval-shaped hollow space, the greater extent of the hollow space preferably runs in the direction of the longitudinal centre axis. One of the advantages of the O-shaped or oval configuration of the hollow space is that, upon insertion of an instrument, the sealing element does not deviate, or deviates only slightly, in the axial direction and thus gives the inserted instrument a better positional stability.

In another preferred embodiment, at least the radially inner wall area of the sealing element has a substantially uniform wall thickness.

Since the radially inner wall area of the sealing element forms the contact surface via which the sealing element bears on an inserted instrument, the substantially uniform wall thickness in this area leads to a uniform deformation of the sealing element and, consequently, leads to the sealing element bearing uniformly and with a good sealing action on the instrument shaft. Compared to the known seals, however, it is not necessary to keep the wall thickness of the sealing element very thin, because the radial extensibility of the sealing element is afforded by the hollow space.

In another preferred embodiment, the radially inner wall area of the hollow space has a thickened part in the shape of an annular bead that is directed radially further inwards.

The thickened part in the shape of an annular bead advantageously strengthens the sealing element in the central area of the radially inner wall area of the sealing element, thus improving the sealing action.

In another preferred embodiment, the sealing body, in the area of at least one of the axial ends, is stiffened by at least one support ring that extends about at least a partial circumference.

The provision of a support ring on at least one of the ends of the sealing body has the advantage that the sealing body as a whole, including the sealing element, can be made of a relatively soft elastomeric material, while the at least one support ring gives the sealing body the necessary shape stability.

It is accordingly preferable if, in the area of both axial ends, the sealing body in each case has at least one support ring that extends about at least a partial circumference.

It is further preferable if the at least one support ring is received in a recess of the sealing body, an external diameter of the at least one support ring being greater than a radial outer diameter of the recess.

This measure has the effect that the support ring radially widens the sealing body at the at least one end, preferably at both ends, as a result of which the sealing body as a whole is narrowed at its waist. This has the advantage of improving the sealing action of the sealing body as such with respect to the housing of the trocar sleeve in which the seal is arranged. The radial widening, present only at the two ends of the sealing body, also makes it easier to replace the seal, since it is only at its axial ends that the sealing body bears with close contact on the inside wall of the trocar head.

In another preferred embodiment, the sealing body is stiffened, in a central area, by at least one central support ring that at least partially surrounds the hollow space from the outside.

The advantage of this is that the radially outwardly directed forces, created when an instrument is guided through the sealing element, do not lead to a radial extension of the sealing body as a whole, and instead only the sealing element is radially extended. A radial escape of the sealing element towards the outside is thus avoided, which further improves the sealing with respect to the instrument.

In another preferred embodiment, the hollow space has, on its radially outer circumference, an annular gap that extends about at least a partial circumference, and the at least one central support ring closes the annular gap.

This measure has the advantage of simplifying the production of the seal in terms of the hollow space that is to be provided, since the latter can initially be formed as an open hollow space from the outside by way of the annular gap, and this annular gap is then closed by means of the at least one central support ring. The central support ring can tightly close the hollow space, for example by means of the central support ring being adhesively bonded into place, or the central support ring is simply placed into the annular gap and, by fitting the seal into the trocar head, the seal is then axially compressed slightly, as a result of which the annular gap is closed by pressure against the central support ring.

In another preferred embodiment, the hollow space communicates with the exterior via at least one opening of small cross section, which opening is preferably provided in the at least one central support ring.

In this embodiment, the hollow space of the sealing element is not completely leaktight per se. Instead, the fluid contained in it can be displaced from the hollow space through the at least one opening and, during relaxation, can pass back into the hollow space. This measure has in particular the advantage that instruments with a large shaft diameter are guided through the seal and cause strong compression of the hollow space. In the case of instruments with a large shaft diameter, it is also not absolutely necessary for the fluid contained in the hollow space to provide the pressure for pressing the radially inner wall area of the sealing element onto the instrument shaft, since, with large shaft diameters of this kind, this contact pressure can be applied already by the elastic wall of the hollow space.

In another preferred embodiment, the sealing element is made of a soft elastomeric material, preferably of silicone.

The use of a soft elastomeric material, in particular silicone, has the advantage that the friction between the instrument shaft and the sealing element is low when the instrument is inserted through the trocar. The sealing element can in particular be formed in one piece with the rest of the sealing body, with the exception of the aforementioned support rings.

The seal can preferably be autoclaved.

The aforementioned support rings and, if appropriate, the central support ring preferably comprise the material PEEK® (polyether ether ketone) and/or a metal.

PEEK® (polyether ether ketone) is stiffer than silicone and is therefore suitable for stiffening the sealing body, as has been described above, and it is also able to be autoclaved. For a particularly high degree of stiffness, the support rings and the central support ring can also be made of a metal, or they can be strengthened by a metal reinforcement.

In another preferred embodiment, the sealing body has a valve, in particular a lip valve.

In addition to having a seal for radial sealing against the instrument shaft, trocar sleeves usually also have a valve that seals the trocar sleeve axially when no instrument is inserted through the trocar sleeve, for example during exchange of instruments. The valves usually constitute separate structural parts. By contrast, the abovementioned embodiment has the advantage that the valve can be produced as a structural unit together with the sealing body, which in particular also simplifies the assembling of the trocar sleeve, since there are fewer individual parts.

It is also preferable if the valve is formed in one piece with the radially inner wall area of the sealing element.

The advantage of this is that the valve, in particular a lip valve, is integrated into the sealing element itself, which advantageously reduces the production costs of a trocar sleeve.

According to another aspect, the invention relates to a trocar sleeve, comprising a tubular shaft, and a trocar head which is arranged at the proximal end of the tubular shaft, and comprising a seal according to one or more of the above embodiments arranged in the trocar head.

Further advantages and features will become clear from the following description and the attached drawing.

It will be appreciated that the aforementioned features and those to be explained below can be used not only in the respectively cited combinations but also in other combinations or singly, without departing from the scope of the present invention.

BRIEF DESCRIPTION OF THE DRAWINGS

Illustrative embodiments of the invention are shown in the drawing and are described in more detail below with reference to the latter. In the drawing:

FIG. 2 shows a longitudinal central section through a trocar head of the trocar sleeve in FIG. 1, on an enlarged scale;

FIGS. 5a) to c) show a seal for use in the trocar in FIG. 1 according to a further illustrative embodiment, with FIG. 5a) showing the seal in a plan view, FIG. 5b) showing the seal in a longitudinal central section along the line Vb-Vb in FIG. 5a), and FIG. 5c) showing the seal in a longitudinal central section along sectional line Vc-Vc in FIG. 5a);

FIG. 6 shows a longitudinal central section through a trocar head in a modification of the illustrative embodiment in FIG. 2; and FIG. 7 shows an enlarged detail B from FIG. 6.

DETAILED DESCRIPTION OF PREFERRED EMBODIMENTS

Figure 1:
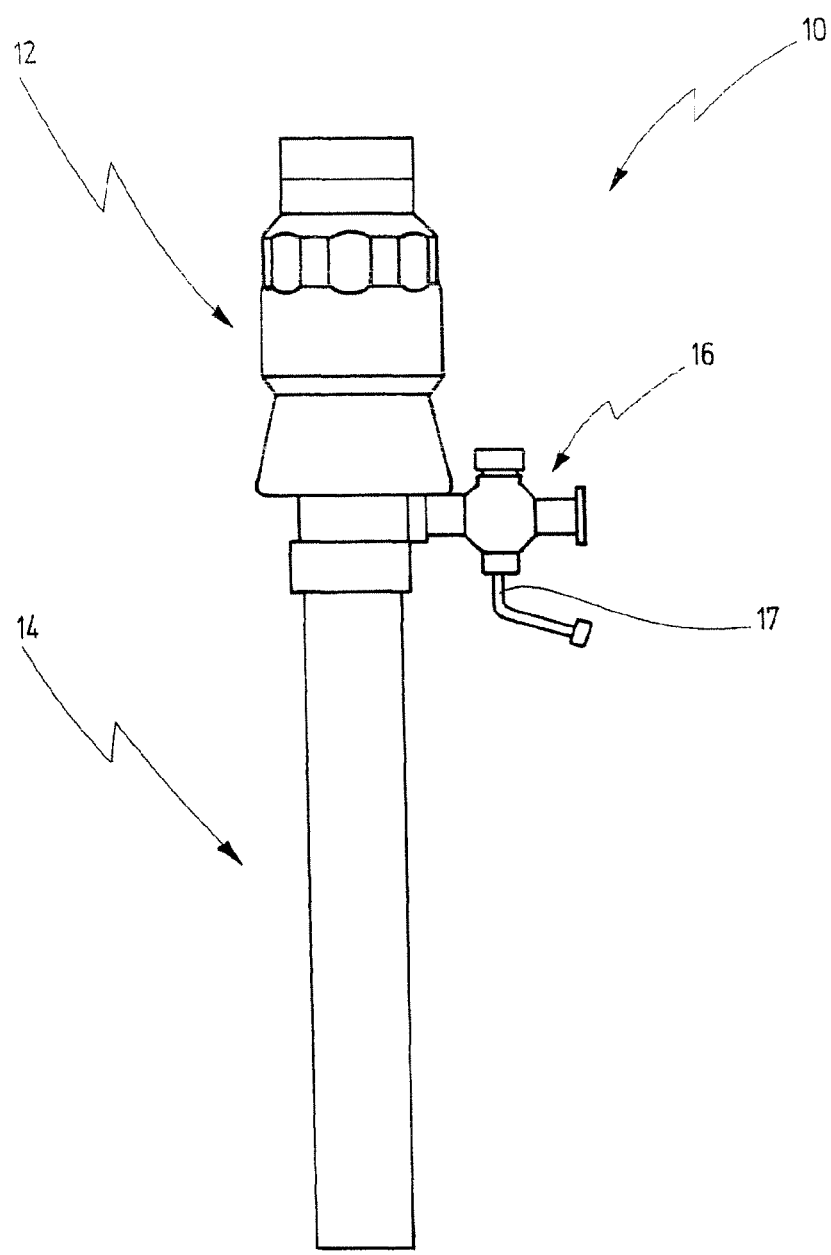
FIG. 1 shows a side view of a trocar sleeve.

In FIG. 1, a trocar sleeve is designated by the general reference number 10. The trocar sleeve 10 is used in minimally invasive surgical procedures for introducing instruments into a body cavity. Together with a trocar mandrel (not shown), the trocar sleeve 10 forms a trocar.

The trocar sleeve 10 has a trocar head 12 and a tubular shaft 14, which is connected releasably to the trocar head 12. A connector piece 16 is also arranged on the trocar head 12, for example for connecting a hose for delivery of an insufflation gas into the body cavity. For opening and closing, the connector piece 16 is provided with a cock 17.

In FIG. 2, the trocar head 12 of the trocar sleeve 10 is shown on its own in a longitudinal central section along a longitudinal centre line 18, and on an enlarged scale compared to FIG. 1.

The trocar head 12 comprises a housing 20 that has a first housing part 22 and a second housing part 24, the two housing parts 22 and 24 being releasably connected to one another via a screwed union 26.

A seal 30, arranged in the first housing part 22, will now be described in more detail with reference to FIGS. 3a) to c).

The seal 30 generally comprises a sealing body 32 which, in the direction of the longitudinal centre axis 18 of the sealing body 32, has a first axial end 34 and a second axial end 36. The sealing body 32 has a circular shape as shown in the plan view in FIG. 3c).

Between the first axial end 34 and the second axial end 36, the sealing body 32 has an elastic sealing element 38. In a radially inner area with respect to the longitudinal centre axis 18, the sealing element 38 defines a passage 40 for an instrument that is to be inserted, as will be described below with reference to FIGS. 4a) to c).

The sealing element 38 has a substantially tubular hollow space 42 that contains a fluid in the form of a gas, in particular air. A radially inner wall area 44 of the sealing element 38, which delimits the hollow space 42 on the radially inner side, i.e. on the side directed towards the longitudinal centre axis 18, surrounds the passage 40 annularly about its complete circumference. The sealing element 38 is accordingly designed as a hollow body.

Figure 3A:
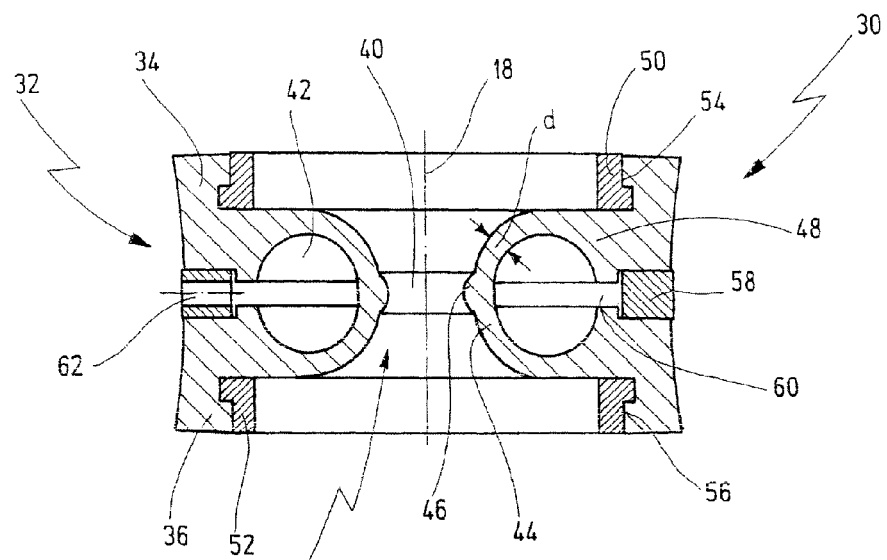
FIGS. 3a) to c) show a seal of the trocar sleeve in FIG. 1 on its own, FIG. 3a) showing the seal in a longitudinal central section along the section line IIIa-IIIa in FIG. 3c) and on an enlarged scale, while FIG. 3b) shows the seal in a side view, and FIG. 3c) shows the seal in a plan view.
Figure 3B:
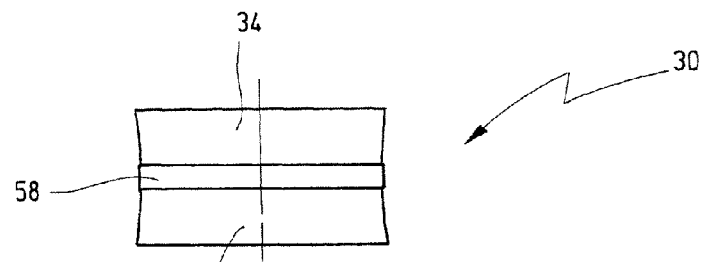

As can be seen from FIG. 3a), the radially inner wall area 44 formed completely about the circumference also has a significant axial extent in the direction of the longitudinal centre axis 18 which, in the illustrative embodiment shown, amounts to approximately two thirds of the total axial extent of the sealing body 32. However, this size is only to be understood as an example.

FIGS. 3a) to c) show the seal 30 in the relaxed state of the sealing element 38, i.e. in a state in which no instrument is guided through the seal 30. In this state, the hollow space 42 in the cross section according to FIG. 3a) assumes an oval shape, the longer dimension of the oval being oriented in the direction of the longitudinal centre axis 18. The radially inner wall area 44 of the sealing element 38 has a substantially uniform wall thickness d. The wall thickness d lies, for example, in a range from approximately 0.8 to approximately 1.3 mm.

The radially inner wall 44 has a convex bulge, as viewed from the longitudinal centre axis 18. The radially inner wall area 44 is also provided with a radially inwardly directed thickened part 46 in the shape of a projecting annular bead.

A radially outer wall area 48 of the sealing element 38 merges into the ends 34 and 36 of the sealing body 32. In particular, the sealing element 38 is designed in one piece with the ends 34 and 36 of the sealing body 32. The radially outer wall area 48 has a larger wall thickness than the radially inner wall area 44, so that the radially outer wall area 48 is more form-stable than the radially inner wall area 44.

The sealing element 38 with the radially inner wall area 44 and the radially outer wall area 48 and the other sections in the area of the ends 34 and 36 of the sealing body 32 are made of a soft elastomeric material, for example silicone.

Figure 3C:
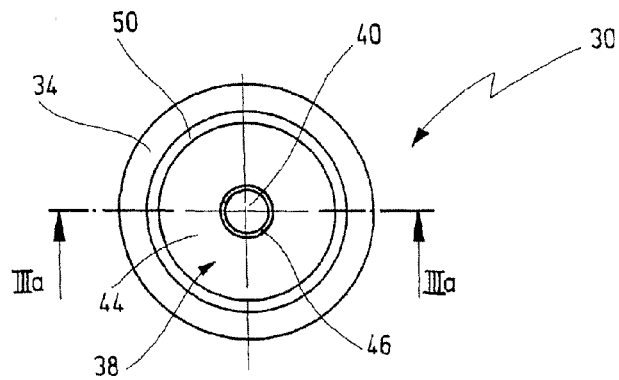

In the area of the two axial ends 34 and 36, the sealing body 32 is stiffened with respective support rings 50 and 52. The support rings 50 and 52 are preferably made of a stiff material, in particular PEEK® (polyether ether ketone) and/or metal. In the illustrative embodiment shown, the support rings 50 and 52 extend about a complete circumference on the seal body 32, as shown in FIG. 3c for the support ring 50.

The support ring 50 is received in a recess of the sealing body 32, an external diameter of the support ring 50 being greater than a radially outer diameter of the recess 54, as a result of which the support ring 50 widens the seal body 32 radially outwards in the area of the end 34.

The support ring 52 is received in a corresponding recess 56 of the sealing body 32 in the area of the second end 36. Here too, the support ring 52 is dimensioned relative to the recess 56 such that the support ring 52 also widens the sealing body 32 radially outwards in the area of the second end 36. Overall, this results in the outer contour of the sealing body 32 being narrowed at the waist, as will be seen from FIGS. 3a) and 3b).

In a middle area between the ends 34 and 36, the sealing body 32 is further stiffened by a central support ring 58. The central support ring 58 is arranged axially at the level of the hollow space 42 of the sealing element 38 and surrounds the hollow space 42 about its complete circumference.

The central support ring 58 thus closes an annular gap 60 which is designed about a complete circumference in the radial outer wall area 48 of the sealing element 38. The hollow space 42 is thus open radially to the outside, which simplifies the manufacture of the sealing body 32 with the sealing element 38. The central support ring 58 not only stiffens the sealing body 32 in the middle area between the ends 34 and 36, but at the same closes the annular gap 60. However, the central support ring 58 does not close the hollow space 42 completely, and instead it leaves a communication, albeit a small one, between the hollow space 42 and the exterior of the hollow space 42 by means of an opening 62 of small cross section, and in the form of a thin bore, being present in the central support ring 58.

In the relaxed state of the sealing element 38 according to FIG. 3a), the fluid, in this case air, is at atmospheric pressure, which is automatically established at all times in the hollow space 42 by way of the opening 62.

Figure 4A:
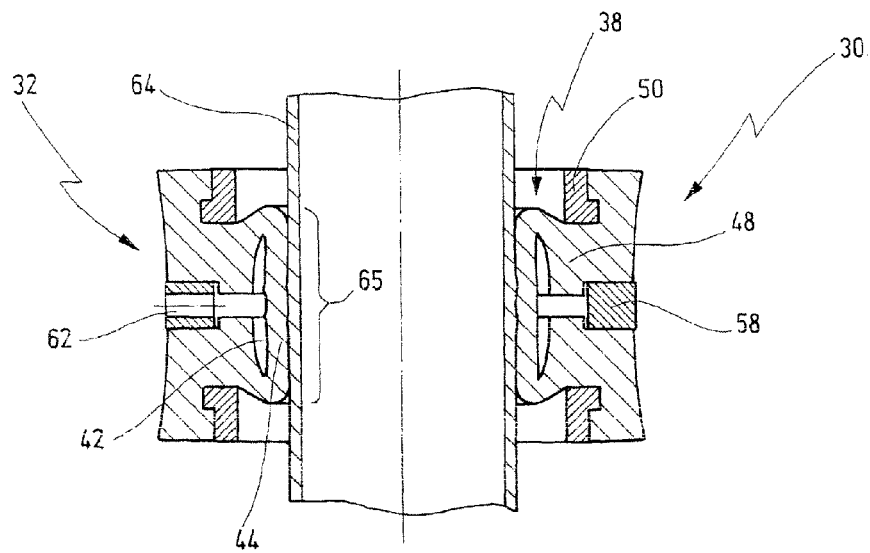
FIGS. 4a) to c) show the seal from FIG. 3 in views corresponding to FIGS. 3a) to 3c), the seal being depicted with an instrument shaft, seen in cross section, extending through the seal.
Figure 4B:
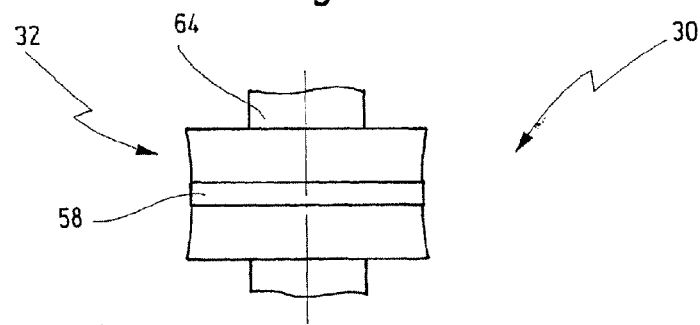
Figure 4C:
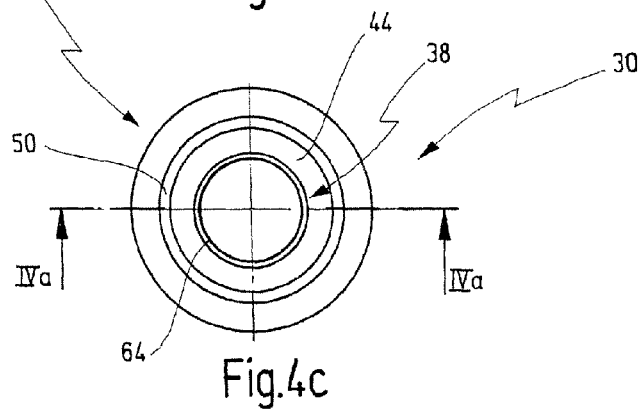

FIGS. 4a) to c) show the seal 30 in a state in which an instrument, of which an instrument shaft 64 is shown in cross section in FIGS. 4a) to c), passes through the seal 30. In this case, the radially inner wall area 44 of the sealing element 38 is deformed, with compression of the hollow space 42, such that the radially inner wall area 44 bears tightly on the instrument shaft 64 along an area 65 that extends considerably in the axial direction. This increases the bearing stability of the instrument in the seal 30. The air contained in the hollow space 42 has been partially displaced out of the opening 62. As is also shown in FIGS. 4a) and 4b), the rest of the sealing body 32 or the radially outer wall area 48 of the sealing element 38 is not deformed, or not appreciably deformed, but instead only the radially inner wall area 44, this being ensured by the central support ring 58. The central support ring 58 thus prevents the sealing element 38 from escaping radially outwards, as a result of which a sufficient pressure force of the radially inner wall area 44 on the instrument shaft is ensured for achieving a high degree of sealing.

After removal of the instrument shaft 64 from the passage 40 in the sealing element 38, the sealing element 38 and in particular the hollow space 42 again adopt the shape according to FIG. 3a), and the hollow space 42 is again filled with air by way of the opening 62.

As FIG. 2 shows, the configuration of the seal 30 in the area of the ends 34 and 36 has the advantage that the sealing body 32 of the seal 30 in the area of the ends 34 and 36 is effectively sealed off relative to the housing 20, i.e. the first housing part 22.

Although the above description has stated that the hollow space 42 of the sealing element 38 is not closed completely tightly, provision can also be made for the hollow space 42 to be completely sealed, in which case the opening 62 in the central support ring 58 or the annular gap 60 in the sealing body 32 are omitted.

Moreover, instead of being filled with air or another gas, the hollow space 42 can be filled with a liquid, for example an oil.

Referring again to FIG. 2, the housing 20 of the trocar head 12 accommodates a valve 66 that seals off the trocar sleeve 10 when no instrument is inserted, as in FIGS. 4a) to c). When the instrument shaft 64 is inserted, the valve 66 is pushed open. In the illustrative embodiment shown in FIG. 2, the valve 66 is designed as a lip valve.

Such a lip valve can, however, also be integrated into the seal 30, as is shown in the illustrative embodiment according to FIGS. 5a) to c).

The seal 30' shown there differs from the seal 30 only in that a valve 66' in the form of a lip valve is arranged in the passage 40' and is designed in one piece with the radially inner wall area 44' of the sealing element 38'. When using the seal 30' instead of the seal 30 in FIG. 2, the valve 66 can thus be omitted, as a result of which, on the one hand, an axially shorter structure of the trocar head 12 is obtained and, on the other hand, fewer parts are needed, as a result of which the assembly work and production costs for the trocar head 12 are reduced.

The rest of the design of the seal 30' corresponds to the seal 30, such that reference may be made to the above description. In FIGS. 5a) to c), identical or similar features have been provided with the same reference numbers, supplemented by a prime mark.

FIGS. 6 and 7 show a further illustrative embodiment of a trocar head 72 which can be connected to the tubular shaft 14 instead of the trocar head 12 in the trocar sleeve 10 in FIG. 1. The trocar head 72 comprises a housing 80 composed of a first housing part 82 and of a second housing part 84. The first housing part 82 and the second housing part 84 are connected to one another by a screwed union 86. An O-ring seal 87 (FIG. 7) ensures additional sealing of the two housing parts 82 and 84 relative to one another. A longitudinal centre axis of the trocar head 72 is provided with the reference label 78.

A seal 90 arranged in the first housing part 82 has a sealing body 92 with a first axial end 94 and a second axial end 96. Between the ends 94, 96, the sealing body 92 has a sealing element 98 with a passage 99, this being designed the same as the sealing element 38 of the seal 30 and in particular having a hollow space 100 with a radially inner wall area 102, as described above.

In contrast to the seal 30, the sealing body 92 is not provided with support rings in the area of the ends 94, 96, and instead it only has a central support ring 104, which is here formed in two parts, namely a plastic ring 105, for example of PEEK® (polyether ether ketone), into which another ring 106, for example of metal, is inserted.

In contrast to the seal 30, the outer contour of the seal 90 is not narrowed at the waist.

A valve 108, which is here designed as a flap valve, is also connected to the seal 90. A holder 110 for the flap valve can be connected fixedly to the sealing body 92 of the seal 90 or be fully integrated therein.

In the outer face of the sealing body 92, retainers (not shown) can be formed that extend axially from the valve 108 to the central support ring 104, in order to secure the valve 108 on the sealing body 92.

What is claimed, is:

1. A seal for a trocar sleeve, comprising:
a sealing body having a longitudinal center axis, a first axial end and a second axial end in direction of said longitudinal center axis, and an elastic sealing element arranged between said first and second ends, said sealing element defining a passage for an instrument in a radially inner area relative to said longitudinal center axis,
said sealing element further having a substantially tubular hollow space, said hollow space having a radially inner wall area that surrounds said passage about its complete circumference to form the passage for the instrument, and a radially outer wall area on a radially outer side relative to said longitudinal center axis of said hollow space, said radially outer wall area having a wall thickness larger than a wall thickness of said radially inner wall area,
said sealing body further having at least one central support ring at least partially surrounding said hollow space on the radially outer wall area of said hollow space and arranged in a central area of said sealing body on the radially outer wall area between the first axial end and the second axial end, said support ring stiffening said sealing body, said sealing body being stiffened by at a first support ring extending about at least a partial circumference of said sealing body and arranged at said first axial end of the sealing body and a second support ring arranged at the second axial end of the sealing body,
wherein said hollow space has an annular gap provided on a radially outer circumference of said hollow space between the first axial end and the second axial end, which extends about at least a partial circumference of said hollow space, and wherein said at least one central support ring is arranged in said annular gap and substantially closes said annular gap,
wherein said first support ring and said second support ring are received in a recess of said sealing body, an external diameter of said first support ring and said second support ring is greater than a radially outer diameter of said recess.

2. The seal of claim 1, wherein said radially inner wall area of said sealing element is bulged convexly, as seen from said longitudinal center axis, when said sealing element is in a relaxed state.

3. The seal of claim 1, wherein said hollow space is substantially O-shaped in a section along said longitudinal center axis.

4. The seal of claim 1, wherein said hollow space is substantially oval in a section along said longitudinal center axis.

5. The seal of claim 1, wherein at least said radially inner wall area of said sealing element has a substantially uniform wall thickness.

6. The seal of claim 1, wherein said radially inner wall area of said sealing element has a thickened part in the shape of an annular bead that is directed radially further inward.

7. The seal of claim 1, wherein said support ring comprises a material selected from the group containing polyether ether ketone and a metal.

8. The seal of claim 1, wherein said sealing element is made of a soft elastomeric material.

9. The seal of claim 8, wherein said elastomeric material is silicone.

10. The seal of claim 1, wherein said sealing body has a valve in said passage for said instrument.

11. The seal of claim 10, wherein said valve is a lip valve.

12. The seal of claim 10, wherein said valve is formed in one piece with said radially inner wall area of said sealing element.

13. A trocar sleeve comprising:
a tubular shaft and a trocar head arranged at a proximal end of said tubular shaft, and comprising a seal, said seal comprising a sealing body having a longitudinal center axis, a first axial end and a second axial end in direction of said longitudinal center axis, and an elastic sealing element arranged between said first and second ends, said sealing element defining a passage for an instrument in a radially inner area relative to said longitudinal center axis,
said sealing element further having a substantially tubular hollow space, said hollow space having a radially inner wall area that surrounds said passage about its complete circumference to form the passage for the instrument, and a radially outer wall area on a radially outer side, relative to said longitudinal center axis of said hollow space, said radially outer wall area having a wall thickness larger than a wall thickness of said radially inner wall area,
said sealing body further having at least one central support ring at least partially surrounding said hollow space on the radially outer wall area of said hollow space and arranged in a central area of said sealing body on the radially outer wall area between the first axial end and the second axial end, said support ring stiffening said sealing body, said sealing body being stiffened by at a first support ring extending about at least a partial circumference of said sealing body and arranged at said first axial end of the sealing body and a second support ring arranged at the second axial end of the sealing body, wherein said hollow space has an annular gap provided on a radially outer circumference of said hollow space between the first axial end and the second axial end, which extends about at least a partial circumference of said hollow space, and wherein said at least one central support ring is arranged in said annular gap and substantially closes said annular gap,
wherein said first support ring and said second support ring are received in a recess of said sealing body, an external diameter of said first support ring and said second support ring is greater than a radially outer diameter of said recess.

14. The seal of claim 1, wherein said hollow space communicating with an environmental exterior of said hollow space via at least one opening, said at least one opening being arranged on said radially outer side of said hollow space and being limited in circumferential direction around said hollow space, said hollow space thereby being under atmospheric pressure when said sealing element being in a relaxed state and when an instrument is passed through said passage defined by said sealing element.

15. The seal of claim 1, wherein said substantially tubular hollow space contains air.

16. The trocar sleeve of claim 13, wherein said hollow space communicating with an environmental exterior of said hollow space via at least one opening, said at least one opening being arranged on said radially outer side of said hollow space and being limited in circumferential direction around said hollow space, said hollow space thereby being under atmospheric pressure when said sealing element being in a relaxed state and when an instrument is passed through said passage defined by said sealing element.

17. The trocar sleeve of claim 13, wherein said substantially tubular hollow space contains air.

18. The seal of claim 1, wherein said at least one central support ring has a thin bore.

19. The trocar sleeve of claim 13, wherein said at least one central support ring has a thin bore.

20. The seal of claim 1, wherein the first support ring and the second support ring widens the sealing body radially outwards.

21. The seal of claim 1, wherein said recess is annular.

* * * * *